(12) United States Patent
Lefort et al.

(10) Patent No.: US 11,791,060 B2
(45) Date of Patent: Oct. 17, 2023

(54) ELUTION PROTOCOLS AND DOSAGES FOR RADIOPHARMACEUTICAL ELUTION SYSTEM

(71) Applicant: Jubilant Draximage Inc., Kirkland (CA)

(72) Inventors: Etienne Lefort, Kirkland (CA); Riccardo Santopietro, Pierrefonds (CA); Robert William Riddoch, Pierrefonds (CA); Paul Donnelly, L'Ile Bizard (CA)

(73) Assignee: Jubilant Draximage Inc.

( * ) Notice: Subject to any disclaimer, the term of this patent is extended or adjusted under 35 U.S.C. 154(b) by 292 days.

(21) Appl. No.: 16/832,436

(22) Filed: Mar. 27, 2020

(65) Prior Publication Data

US 2020/0312474 A1 Oct. 1, 2020

Related U.S. Application Data

(60) Provisional application No. 62/826,711, filed on Mar. 29, 2019.

(51) Int. Cl.
*G21G 1/00* (2006.01)
*A61M 5/00* (2006.01)
*A61M 5/14* (2006.01)
*A61M 5/142* (2006.01)

(52) U.S. Cl.
CPC ............ *G21G 1/0005* (2013.01); *A61M 5/007* (2013.01); *A61M 5/14* (2013.01);
(Continued)

(58) Field of Classification Search
CPC ......... G21G 1/0005; G21G 2001/0031; G21G 4/08; G21G 1/001; A61K 51/1282;
(Continued)

(56) References Cited

U.S. PATENT DOCUMENTS 6,440,386 B1 * 8/2002 Leung ................. A61K 51/088
424/1.53
7,331,340 B2 * 2/2008 Barney ............. A61M 15/0091
128/200.23
(Continued)

FOREIGN PATENT DOCUMENTS

CA 2884077 A1 * 3/2014
WO WO-2004105049 A1 * 12/2004
(Continued)

*Primary Examiner* — Nilay J Shah
(74) *Attorney, Agent, or Firm* — BakerHostetler (57) ABSTRACT

A radioisotope elution system is provided. The radioisotope elution system may comprise a controller that is configured to calculate the available amount of daughter radioisotope at any time during establishment of the equilibrium for decay of the parent radioisotope into its daughter radioisotope. The radioisotope elution system may comprise a controller that is configured to schedule various patient infusions planned for the next following days and weeks in accordance with the available amount of daughter radioisotope on each day. The elution system may also comprise a controller that is connected to the imaging software of a radioisotope imaging device, where the radioisotope imaging device is arranged for imaging the patient or a region of the patient; and the controller is configured to start an image acquisition at a predetermined time.

16 Claims, 2 Drawing Sheets

(52) U.S. Cl.
CPC ............ *A61M 2005/14208* (2013.01); *A61M 2205/3334* (2013.01); *A61M 2205/3337* (2013.01); *A61M 2205/502* (2013.01); *A61M 2205/581* (2013.01); *A61M 2205/583* (2013.01); *A61M 2210/0693* (2013.01); *A61M 2210/08* (2013.01); *A61M 2210/1082* (2013.01); *A61M 2210/125* (2013.01); *G21G 2001/0031* (2013.01)

(58) Field of Classification Search
CPC ......... G16H 20/17; A61M 5/007; A61M 5/00; A61M 5/14; A61M 2005/14208; A61M 2205/3334; A61M 2205/3337; A61M 2205/502; A61M 2205/505; A61M 2205/507; A61M 2205/52; A61M 2205/581; A61M 2205/58; A61M 2205/583; A61M 2205/584; A61M 2205/582; A61M 2210/0693; A61M 2210/08; A61M 2210/1082; A61M 2210/125

See application file for complete search history.

(56) References Cited

U.S. PATENT DOCUMENTS

| | | | |
|---|---|---|---|
| 2007/0213848 A1* | 9/2007 | deKemp | G05B 13/024 |
| | | | 700/32 |
| 2008/0242915 A1* | 10/2008 | Jackson | G21F 5/018 |
| | | | 600/4 |
| 2009/0309466 A1* | 12/2009 | Quirico | G21G 1/0005 |
| | | | 312/209 |
| 2012/0285294 A1* | 11/2012 | Shanks | G21G 1/0005 |
| | | | 75/393 |
| 2015/0260855 A1 | 9/2015 | Mcquaid et al. | |

FOREIGN PATENT DOCUMENTS

| | | |
|---|---|---|
| WO | WO-2008134578 A2 * | 11/2008 |
| WO | WO-2009152320 A2 * | 12/2009 |
| WO | WO-2009152326 A2 * | 12/2009 |
| WO | 2014/036627 A1 | 3/2014 |
| WO | WO-2014036627 A1 * | 3/2014 |

* cited by examiner

ELUTION PROTOCOLS AND DOSAGES FOR RADIOPHARMACEUTICAL ELUTION SYSTEM

CROSS-REFERENCE TO RELATED APPLICATIONS

The present application claims the benefit of priority to U.S. Provisional Application Ser. No. 62/826,711, filed Mar. 29, 2019, the entire contents of which are incorporated herein by reference.

TECHNICAL FIELD

The present invention relates in general to nuclear medicine and, in particular, to radiopharmaceutical medical devices for the generation of a radiopharmaceutical composition for treating and/or diagnosing a disease or a condition.

BACKGROUND

Radioisotopes play a pivotal role in diagnosis and mitigation of various diseased conditions. For example, $^{60}$Co in treatment of cancer, $^{131}$I in treatment of hyperthyroidism, $^{14}$C in breath tests, $^{99m}$Tc and $^{82}$Rb as tracers in myocardial perfusion imaging. The radioisotopes for pharmaceutical use are produced either by nuclear bombardment in cyclotron in specially approved remote sites or in-situ by employing radioisotope generators at the site of use.

Rubidium ($^{82}$Rb) is used as a positron emission tomography (PET) tracer for non-invasive measurement of myocardial perfusion. Rubidium-82 is produced in situ by radioactive decay of strontium-82. Rubidium elution systems utilize doses of rubidium-82 generated by elution within a radioisotope generator, and infuse the radioactive solution into a patient. The infused dose of radiopharmaceutical is absorbed by cells of a target organ of the patient and emit radiation which is detected by a PET scanner in order to generate an image of the organ.

There is a need to improve the dosage of infused pharmaceutical, and increase the number of patients that can be diagnosed/treated per day with minimal waiting time and radiation exposure.

SUMMARY

The present invention aims to provide elution systems that maximize the usage of parent radioisotope and minimize the recharge time between two successive elutions.

The present invention also aims to provide the minimal and adequate dose of radiopharmaceutical to a patient.

It is an object of the present invention to determine the minimal regeneration time between two successive elutions of specific doses.

It is also an object of the present invention to maximize the usage of parent isotope present in the generator system.

It is another object of the present invention to minimize the radiation exposure to the patients.

It is yet another object of the present invention to minimize the waiting time between elutions. The present invention concerns any of the following items:

1. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller for controlling the pump; wherein the system is characterized in that:
   the controller is configured to calculate a real time amount of daughter radioisotope that is available in the generator during the establishment of an equilibrium for decay of the parent radioisotope into its daughter radioisotope; and
   the controller provides real time information during establishment of the equilibrium, said information comprising the available amount of daughter radioisotope that can be infused to the patient.
2. The radioisotope elution system of item 1, wherein the real time information further comprises the flow rate of infusion that is requested to infuse said available amount, and/or the duration of infusion that is requested to infuse said available amount.
3. The radioisotope elution system of item 1 or 2, wherein the system further comprises a user interface, and wherein the controller displays the real time information on the interface.
4. The radioisotope elution system of item 3, wherein the available amount of daughter radioisotope is displayed in terms of activity dose unit.
5. The radioisotope elution system of any one of items 1 to 4, wherein the controller is further configured to calculate the time lapsed until the establishment of an equilibrium for decay of the parent radioisotope into its daughter radioisotope.
6. The radioisotope elution system of item 5, wherein the controller provides the information about the time lapsed until the establishment of the equilibrium.
7. The radioisotope elution system of any one of items 1 to 6, wherein the controller notifies a user of the system immediately once the available amount of daughter radioisotope reaches a needed amount that the user has entered into the system.
8. The radioisotope elution system of item 7, wherein the notification is audible or visual, or both.
9. The radioisotope elution system of any one of items 1 to 8, wherein the daughter radioisotope is rubidium-82.
10. The radioisotope elution system of any one of items 1 to 9, wherein a following patient infusion is pre-programmed and wherein the controller starts a patient infusion corresponding to said pre-programmed patient infusion automatically when the available amount of daughter radioisotope in the generator has reached a sufficient amount for infusing the following pre-programmed patient infusion.
11. The radioisotope elution system of any one of items 1 to 10, wherein the system further comprises:
   a generator line by which the eluate exits the generator;
   a tubing line system that directs the eluant from the eluant reservoir to the generator, wherein the tubing line system comprises a first valve that directs alternatively the eluant to the generator or a bypass line, wherein the bypass line is merged with a generator line at a merging point;
   wherein the system further comprises a radioactivity detector downstream the merging point for detecting the radioactivity of a mixture of an eluate generated by the generator and the eluant directed by the bypass line;
   wherein the controller controls the first valve and the pump for adjusting:
   i) the radioactivity per volume at the merging point, or ii) a flow rate of the mixture at the merging point, or
iii) both.
12. The radioisotope elution system of item 11, wherein the radioactivity per volume or the flow rate is determined in accordance with the patient requirement.
13. The radioisotope elution system of item 12, wherein the patient requirement is based on at least one characteristic of the patient, said at least one characteristic of the patient is age, sex, body weight, body mass index, body circumference and/or a surface area.
14. The radioisotope elution system of item 12, wherein the patient requirement is based on the organ or the part of the patient that is intended for imaging.
15. The radioisotope elution system of item 14, wherein the organ or the part of the patient is heart, brain, kidney, limb or blood vessel; and wherein the daughter radioisotope is rubidium-82.
16. The radioisotope elution system of any one of items 1 to 15, wherein the system further comprises a radioisotope imaging device for imaging the patient or an organ or a part of the patient; wherein the controller is connected to an imaging software of the radioisotope imaging device.
17. The radioisotope elution system of item 16, wherein the controller is configured to start an image acquisition at a predetermined time after the patient infusion has begun or has ended.
18. The radioisotope elution system of any one of items 1 to 17, wherein the system further comprises a tubing system interconnecting the radioisotope elution system with a stress agent reservoir, wherein the controller is configured to control the infusion of a stress agent contained in the stress agent reservoir to the patient.
19. The radioisotope elution system of item 18, wherein the stress agent infusion is performed at a predetermined time prior to infusing the daughter radioisotope eluate to the patient.
20. The radioisotope elution system of item 18 or 19, wherein the stress agent infusion is automated and the controller controls the dose of stress agent and the pre-determined time prior to infusing a patient with a daughter radioisotope eluate.
21. The radioisotope elution system of item 20, wherein the dose of stress agent is determined in accordance with the patient requirement.
22. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller for controlling the pump, and a user interface; wherein the system is characterized in that:
the controller is configured to calculate an amount of daughter radioisotope that is available in the generator for a patient infusion and estimate the amount of daughter radioisotope that will be available in the generator the following days;
the controller is configured to receive information from the user about the patient infusions that are intended; and
the controller is configured to display on the interface a recommended day for infusing each of the patient infusions that are intended.
23. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, and a controller for controlling the pump; wherein the system is characterized in that:
the system further comprises a radioisotope imaging device for imaging the patient or an organ or a part of the patient; and
the controller is connected to an imaging software of the radioisotope imaging device.
24. The radioisotope elution system of item 23, wherein the controller is configured to start an image acquisition at a predetermined time after the patient infusion has begun or has ended.
25. The radioisotope elution system of item 23 or 24, wherein the system further comprises a tubing system interconnecting the radioisotope elution system with a stress agent reservoir, wherein the controller is configured to control the infusion of a stress agent contained in the stress agent reservoir to the patient.
26. The radioisotope elution system of item 25, wherein the stress agent infusion is performed at a predetermined time prior the daughter radioisotope eluate infusion.
27. The radioisotope elution system of item 25 or 26, wherein the stress agent infusion is automated and the controller controls the dose of stress agent and the pre-determined time prior to infusing a patient with a daughter radioisotope eluate.
28. The radioisotope elution system of item 27, wherein the dose of stress agent is determined in accordance with the patient requirement.
29. The radioisotope elution system of item 28, wherein the patient requirement is based on at least one characteristic of the patient, said at least one characteristic of the patient is age, sex, body weight, body mass index, body circumference and/or a surface area.
30. The radioisotope elution system of item 28, wherein the patient requirement is based on the organ or the part of the patient that is intended for imaging.
31. The radioisotope elution system of item 30, wherein the organ or the part of the patient is heart, brain, kidney, limb or blood vessel; and wherein the daughter radioisotope is rubidium-82.

BRIEF SUMMARY OF DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

The present invention can be more readily understood by reading the following detailed description of the invention and included embodiments.

As used herein, the term "column" refers to the functional component of a radiopharmaceutical generator, wherein a hollow column made up of a radiation resistant material is packed with an ion exchange resin, wherein the ion exchange resin is loaded or charged with parent radioisotope. The ion exchange resin has higher affinity for parent radioisotope as compared to daughter radioisotope. Thus, on elution with a suitable medium, daughter radioisotope gets eluted from the generator while parent radioisotope stays adsorbed to matrix of ion exchange resin. The daughter radioisotope is formed in-situ by radioactive decay of parent radioisotope in the column.

As used herein, the term "generator system" or "generator" or "radioisotope generator" refers to one or more columns containing radioisotope in a shielded container wherein a radiation shielding material surrounds the columns in order to absorb the energy radiating from the generator container, thus protecting the end user from getting exposed to harmful radiation. The radioisotopes which can be used with radioisotope generator include, but are not limited to $^{99}Mo/^{99m}Tc$, $^{90}Sr/^{90}Y$, $^{82}Sr/^{82}Rb$, $^{188}W/^{188}Re$, $^{68}Ge/^{68}Ga$ $^{42}Ar/^{42}K$, $^{44}Ti/^{44}Sc$, $^{52}Fe/^{52m}Mn$, $^{72}Se/^{72}As$, $^{83}Rb/^{83m}Kr$; $^{103}Pd/^{103m}Rh$, $^{109}Cd/^{109m}Ag$, $^{113}Sn/^{113m}In$, $^{118}Te/^{118}Sb$, $^{132}Te/^{132}I$, $^{137}Cs/^{137m}Ba$, $^{140}Ba/^{140}La$, $^{134}Ce/^{134}La$, $^{144}Ce/^{144}Pr$, $^{140}Nd/^{140}Pr$, $^{166}Dy/^{166}Ho$, $^{167}Tm/^{167m}Er$, $^{172}Hf/^{172}Lu$, $^{178}W/^{178}Ta$, $^{191}Os/^{191m}Ir$, $^{194}Os/^{194}Ir$, $^{226}Ra/^{222}Rn$ and $^{225}Ac/^{213}Bi$.

As used herein, the term "radioisotope regeneration time" or "regeneration time" or "idle time" or "recharge time" refers to the time required for generator system to establish an equilibrium between rate of production of daughter radioisotope and rate of decay of daughter radioisotope. Once the radioisotope has been eluted out from the column, the generator cannot be used again instantly. The generator needs some time for formation of daughter radioisotope by radioactive decay of parent radioisotope and for establishment of equilibrium between rate of production of daughter radioisotope and rate of decay of daughter radioisotope.

As used herein, the terms "medical unit" or "radioisotope medical unit", or "radioisotope medical device" or "radioisotope elution device" are used interchangeably. In an embodiment, it refers to elution system contained in cabinet structures. Optionally, the medical unit can be carried by a mobile cart.

As used herein, the term "elution system" refers to infusion system meant for generating a solution containing radioisotopes, measuring the radioactivity in the solution, and infusing the solution into a patient.

As used herein, the term "Sr/Rb elution system" or "$^{82}Sr/^{82}Rb$ elution system" refers to infusion system meant for generating a solution containing $^{82}Rb$, measuring the radioactivity in the solution, and infusing the solution into a patient in order to perform various studies on the patient's heart.

As used herein, the term "shielded components" refers to components that are shielded by a radiopaque material. The "shielded components" may include, for instance, a generator, a dose calibrator, an activity detector and/or a waste container. The terms "waste reservoir" and "waste container" are interchangeably used herein.

As used herein, the term "shielded" refers to the condition of being housed within a compartment that provides a barrier to radioactive radiation generated by the radioisotope. The shielding prevents radiation hazard and exposure of an operator or user to unwanted radiation. Said shielding may be made up of any radiation attenuating material including but not limited to depleted uranium (U), lead (Pb), tin (Sn), antimony (Sb), tungsten (W), bismuth (Bi) or any other suitable element or material and any combination thereof.

As used herein, the term "non-shielded components" refers to pump system, valve system, saline reservoir, computer system and/or controller.

As used herein, the term "eluant" refers to the liquid or the fluid used for selectively leaching out the daughter radioisotopes from the generator column.

As used herein, the term "eluate" refers to the radioactive eluant after acquisition of daughter radioisotope from the generator column.

In an embodiment, the present invention concerns a radiopharmaceutical elution system comprising a suitable eluant contained in an eluant reservoir, a radioactive generator containing a parent radioisotope that decays into a corresponding daughter radioisotope, a first tubing line interconnecting the eluant reservoir and the generator, a pump for pumping the eluant from the eluant reservoir through said first tubing line, a first valve located on said tubing line and downstream the pump for directing the eluant to the generator or to a by-pass line, an eluate exiting the generator through a second tubing line and containing the daughter radioisotope, the second tubing line having a connection to receive the eluant from the by-pass line, a radioactivity detector on the second tubing line downstream said connection, a second valve on the second tubing line downstream the detector for directing the eluate to a patient line or to a waste line that is connected to a waste reservoir, the patient line is adapted for infusion into a patient, a controller for controlling the pump, the first valve and the second valve, and for receiving the information from the detector.

Figure 1:
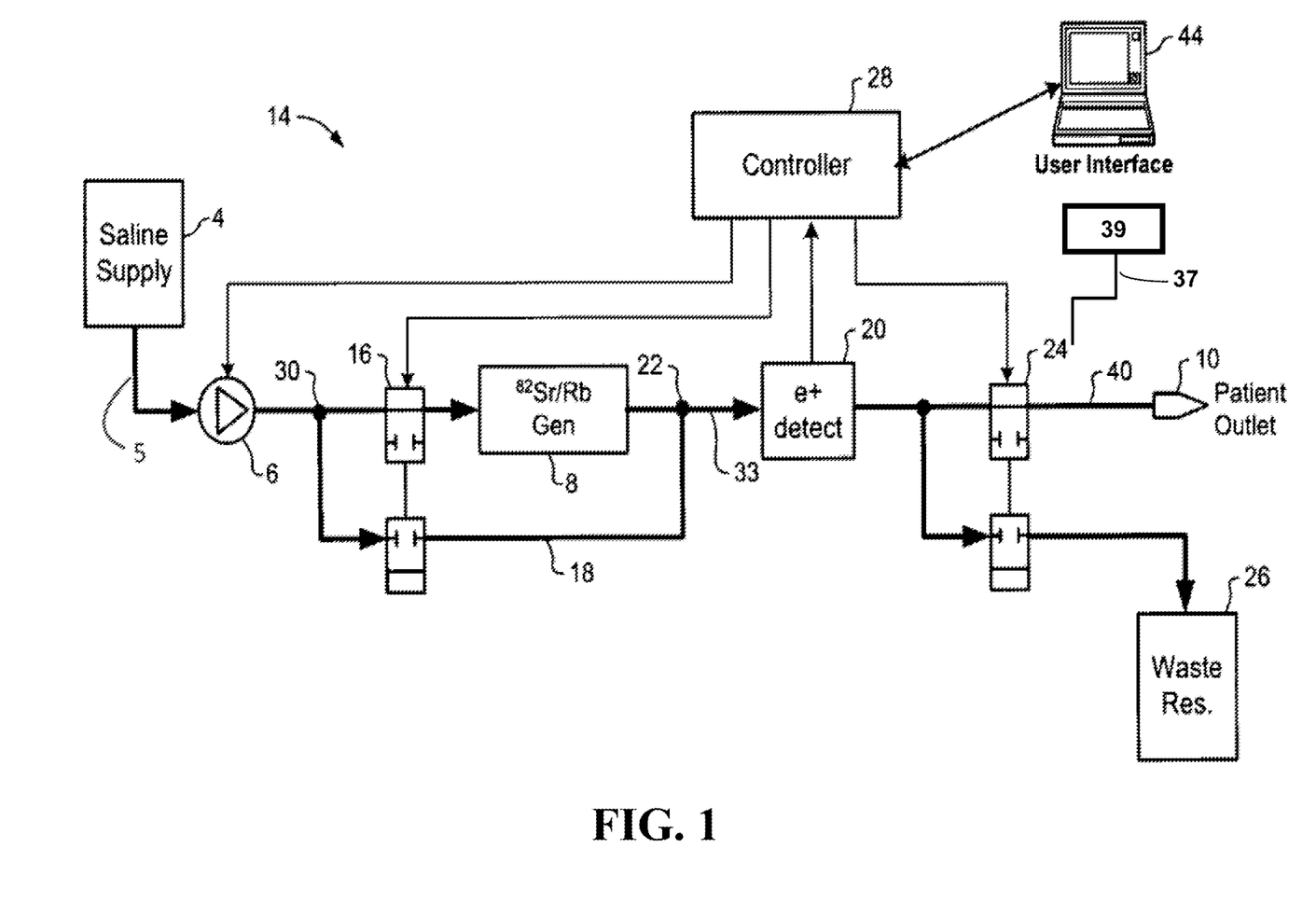
FIG. 1 is a block diagram schematically illustrating principal elements of a Rubidium elution system in accordance with an embodiment of the present invention.

In an embodiment, the radiopharmaceutical elution system is a rubidium ($^{82}Rb$) elution system, which comprises the components described in FIG. 1. In an embodiment, the elution system comprises reservoir 4 of sterile saline solution (e.g. 0.9% Sodium Chloride Injection); a pump 6 for drawing saline from the reservoir 4 through the supply line 5 and the generator line (between 30 and 22) at a desired flow rate; a generator valve 16 for proportioning the saline flow between a strontium-rubidium ($^{82}Sr/^{82}Rb$) generator 8 and a bypass line 18 which circumvents the generator 8; a positron detector 20 located downstream of the merge point 22 at which the generator and bypass flows merge and from which fluid flow travels via fluid line 33 to the positron detector 20; and a patient valve 24 for controlling supply of active saline to a patient outlet 10 via patient line 40 and to a waste reservoir 26. A controller 28 in communication with a user interface computer 44 is preferably connected to the pump 6, positron detector 20 and valves 16 and 24 to control the elution system 14 in accordance with a desired control algorithm.

Figure 2:
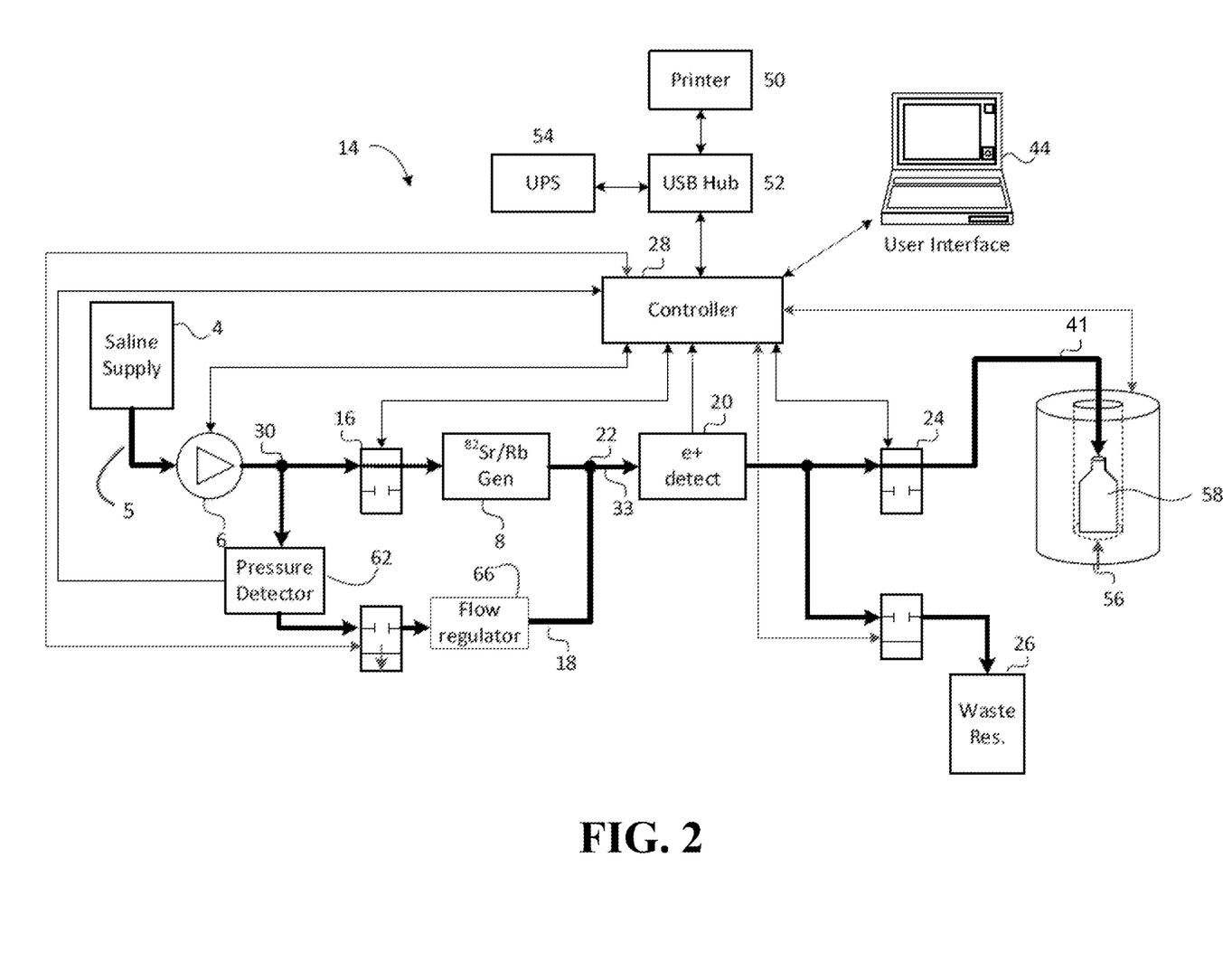
FIG. 2 is a block diagram schematically illustrating principal elements of a Rubidium elution system in accordance with another embodiment of the present invention.

FIG. 2 is a block diagram schematically illustrating principal elements of a Rubidium elution system in accordance with another embodiment of the present invention. The Rubidium elution system of FIG. 2 has similar elements as the Rubidium elution system of FIG. 1, and additional elements. These additional elements preferably include one or more of a printer 50 and USB (Universal Serial Bus; or other communications port) port 52, a pressure detector 62, an eluate line 41, a dose calibrator 56, a flow regulator 66, or a UPS (Uninterruptible Power Supply) 54.

The Rubidium elution system of FIG. 2 may be used to assess various aspects of the system, such as a concentration of $^{82}Rb$, $^{82}Sr$, or $^{85}Sr$ in a fluid that is eluted from the generator, the volume of the fluid that is eluted from the generator, or the pressure of the fluid flowing through at least one portion of the system. Information about these aspects of the system may be gathered by various elements of the system, and sent to the controller. The controller 28 and/or user interface computer 44 (which may comprise a processor and memory) may analyze this gathered data to assess the state of the system.

As shown in FIG. 2, the pressure detector 62 is configured to detect the in-line pressure of the bypass line, and to convey information about this pressure to the controller. The pressure detector may be configured to detect the in-line pressure elsewhere within the system, such as the feed-line (saline supply-line).

The user interface computer 44 is depicted as being connected to a printer 50, and having a USB port. The user interface of the user interface computer 44 may be used to generate an output on the user interface based on a result of the assessment. The printer 50 may be used to print out information about the state of the system, such as a activity of $^{82}$Rb, $^{82}$Sr, or $^{85}$Sr in a fluid that is eluted from the generator, the flow rate of the fluid that is eluted from the generator, or the pressure of the fluid flowing through at least one portion of the system. The USB port may be used to store an indication of the result of the assessment in a memory location, such as a flash drive.

The elution system of FIG. 2 may additionally have a dose calibrator 56 that receives eluate via eluate line 41. The dose calibrator 56 may be used instead of a patient outlet, or in addition to a patient outlet, along with a valve that may be configured to direct fluid to the patient outlet or to the dose calibrator. The dose calibrator 56 may comprise a vial 58 (such as a 50 mL vial) that collects the fluid as it otherwise exits the elution system. The dose calibrator 56 may be communicatively coupled to the controller 28, and configured to send information to the controller 28, such as an activity concentration of $^{82}$Rb, $^{82}$Sr, or $^{85}$Sr in a fluid that is eluted from the generator. The dose calibrator 56 may include a radioactivity shielding material.

In certain embodiments, the system is embodied in a portable (or mobile) cart that houses some or all of the generator, the processor, the pump, the memory, the patient line, the bypass line, the positron detector, and/or the calibrator. In an embodiment, the system may contain a "primary cart" and a "secondary cart". Each cart can be mobile or stationary. As used herein, the term "primary cart" refers to the first cart comprising components of the elution system such as a generator, an eluant reservoir, a pump, and/or a waste reservoir. The primary cart preferably comprises a shielding assembly located within a primary cabinet. As used herein, the term "secondary cart" refers to the second cart comprising other components such as a dose calibrator. The secondary cart preferably comprises a shielding assembly located within a second cabinet.

As used herein, the term "cabinet" refers to the outer structure stretching upward from platform surface of cart wherein the cabinet structure house all the shielded and non-shielded components of the system. The cabinet structure may be made up of any of the radiation resistant material including but not limited to stainless steel, injection-molded polyurethane or any other suitable materials and combinations thereof fitted together according to methods known to those skilled in the art. In an embodiment, the cabinet can be made of a shielding material.

As used herein, the term "quality control test" refers to the tests performed on daily basis for evaluating the safety and efficacy of elution system and more precisely the generator system. If any of the quality control tests fail, then the generator system is configured to not perform a patient elution. Quality control measures may include, but are not limited to, checking and/or testing the status of each of the columns, breakthrough testing on at least one column, flow rate, leakage, column and tubing pressure, eluant volume, waste bottle volume, eluate reservoir volume, activity of parent and daughter isotopes, sensors, pump and valves functioning, checking the environment surrounding elution system, testing outputs produced by each of the columns, and/or performing testing on samples of the radiopharmaceuticals produced by columns, among other quality control measures. Quality control system may be used to generate one or more quality reports relating to the quality of the radiopharmaceuticals produced by the elution system. Quality reports may include, but are not limited to: analytical tests performed on the product; total yield of the products; failure reports for the product; failure reports for the one or more systems used to manufacture the product; and/or operator error reports, among other quality reports. Quality control system may interface with each individual system when performing the quality control tests.

In an embodiment, the radiopharmaceutical elution system comprises at least a radioisotope generator, a patient line for infusing a patient with a radioisotope eluate generated by the generator, an eluant reservoir, a pump for pumping eluant from the eluant reservoir to the generator, a controller for controlling the pump.

In an embodiment, the radiopharmaceutical elution system comprises a suitable eluant contained in an eluant reservoir, a radioactive generator containing a parent radioisotope that decays into a corresponding daughter radioisotope, a first tubing line interconnecting the eluant reservoir and the generator, a pump for pumping the eluant from the eluant reservoir through said first tubing line, a first valve located on said tubing line and downstream the pump for directing the eluant to the generator or to a by-pass line, an eluate exiting the generator through a second tubing line and containing the daughter radioisotope, the second tubing line having a connection to receive the eluant from the by-pass line, a radioactivity detector on the second tubing line downstream said connection, a second valve on the second tubing line downstream the detector for directing the eluate to a patient line or to a waste line that is connected to a waste reservoir, the patient line is adapted for infusion into a patient, a controller for controlling the pump, the first valve and the second valve, and for receiving the information from the detector, wherein the controller is connected to an imaging software of a radioisotope imaging device that is arranged for imaging the patient receiving the radioisotope infusion or a region of said patient.

In an embodiment of the invention, the controller preferably allows a patient infusion before establishment of said equilibrium; and preferably once the generator recharge level is sufficient to provide a dose required for a specific patient infusion. Generally, 90% of the regeneration is reached within 5 minutes and complete regeneration is reached after 10 minutes. Therefore, a patient elution can be possible after 4, 5, 6, 7 8 or 9 minutes, and preferably after 5 or 6 minutes.

In an embodiment of the invention, the radioisotope elution system comprises at least a radioisotope generator containing a parent radioisotope that decays into a daughter radioisotope, a patient line for infusing a patient with a daughter radioisotope eluate generated by the generator, a pump for pumping an eluant from an eluant reservoir into the generator, and a controller for controlling the pump. In a preferred embodiment, the controller of the radioisotope elution system is configured to calculate a real time amount of daughter radioisotope that is available in the generator during the establishment of an equilibrium for decay of the parent radioisotope into its daughter radioisotope. Preferably, the controller provides real time information at each instant during establishment of the equilibrium. This real time information comprises at least the available amount of daughter radioisotope that can be infused to the patient. In an embodiment, the real time information further comprises the flow rate of infusion that is requested to infuse said available amount, and/or the duration of infusion that is requested to infuse said available amount. The user is enabled to select the desired dose, flow rate and duration of infusion. However, this embodiment of the elution system advantageously provides guidance the user to start a patient elution as soon as the desired amount of daughter radioisotope is available, even when the generator is not completely recharged (i.e. when the equilibrium of the decay of the parent radioisotope into the daughter radioisotope is not completely attained or established). This feature is particularly useful in a situation when a stress agent was administered to the patient and the infusion of daughter radioisotope was interrupted or delayed for any reason, since the daughter radioisotope has to be infused to the patient before the end of the efficacy of the stress agent and this end of efficacy may occur before establishment of the equilibrium. Therefore, the real time information on the available amount of daughter radioisotope allows the user to start a patient elution as soon as the desired dose is available and prior to the end of efficacy of the stress agent. The end of efficacy of the stress agent usually depends on the nature of the stress agent, but may also be influenced by the dose of stress agent that was administered to the patient and the patient characteristic in certain circumstances. In an embodiment, the radioisotope elution system further comprises a user interface, which advantageously displays the real time information provided by the controller. The available amount of daughter radioisotope can be displayed in terms of activity dose unit (mCi) or in terms of percentage of the desired dose to be eluted by the user. In an embodiment, the controller provides a notification to the user immediately once the available amount of daughter radioisotope reaches a needed amount (or desired dose) that the user has previously entered into the system. This notification can be audible or visual, or both.

In an embodiment, the controller of the radioisotope elution system is also configured to calculate the time that remains for the equilibrium for decay of the parent radioisotope into its daughter radioisotope is reached or established. This information about the time lapsed until the establishment of the equilibrium is advantageously provided to the user by the controller.

In any of the embodiments disclosed herein, the daughter radioisotope is preferably rubidium-82.

In another embodiment of the present invention, the following patient infusion can be pre-programmed in the radioisotope elution system and the controller advantageously starts a patient infusion corresponding to said pre-programmed patient infusion automatically when the available amount of daughter radioisotope in the generator has reached a sufficient amount for infusing the following pre-programmed patient infusion. This feature advantageously allows the next patient infusion to start without any waste of time.

In another embodiment, the radioisotope elution system further comprises a generator line by which the eluate exits the generator, and a tubing line system that directs the eluant from the eluant reservoir to the generator. Said tubing line system preferably comprises a first valve that directs alternatively the eluant to the generator or a bypass line. The bypass line is preferably merged with a generator line at a merging point. The system preferably further comprises a radioactivity detector downstream the merging point for detecting the radioactivity of a mixture of an eluate generated by the generator and the eluant directed by the bypass line. The controller of the system preferably controls the first valve and the pump for adjusting: i) the radioactivity per volume at the merging point, or ii) a flow rate of the mixture at the merging point, or iii) both. Preferably, the radioactivity per volume and/or the flow rate is determined in accordance with the patient requirement. This patient requirement is preferably based on at least one characteristic of the patient, such as age, sex, body weight, body mass index, body circumference and/or a surface area. This patient requirement may also be based on the organ or the part of the patient that is intended for imaging. Said organ or part of the patient can be the heart, the brain, the kidneys, a limb or the blood vessels; when the daughter radioisotope is rubidium-82.

In another embodiment, the radioisotope elution system further comprises a radioisotope imaging device for imaging the patient or an organ or a part of the patient, and the controller is connected to an imaging software of the radioisotope imaging device. In an aspect of this embodiment, the controller is preferably preconfigured to start an image acquisition at a predetermined time after the patient infusion has begun or has ended.

In another embodiment, the radioisotope elution system further comprises a tubing system 37 interconnecting the radioisotope elution system with a stress agent reservoir 39. In an aspect of this embodiment, the controller 28 is preferably configured to control the infusion of a stress agent contained in the stress agent reservoir to the patient. The stress agent infusion is preferably performed at a predetermined time prior to infusing the daughter radioisotope eluate to the patient. In another preferred aspect of this embodiment, the stress agent infusion is automated and the controller 28 controls the dose of stress agent and the predetermined time prior to infusing a patient with a daughter radioisotope eluate. The dose of stress agent can be determined in accordance with the patient requirement. Said patient requirement is based on at least one characteristic of the patient, such as age, sex, body weight, body mass index, body circumference and/or a surface area. Said patient requirement may also be based on the organ or the part of the patient that is intended for imaging. The organ or part of the patient is preferably the heart, the brain, the kidneys, a limb or the blood vessels, when the daughter radioisotope is rubidium-82.

In a further embodiment of the present invention, the controller of the radioisotope elution system is advantageously configured to calculate an amount of daughter radioisotope that is available in the generator for a patient infusion and estimate the amount of daughter radioisotope that will be available in the generator the following days. The controller is preferably configured to receive information from the user about the patient infusions that are intended to be performed in the next following days or weeks. The controller is advantageously configured to display on the interface a recommended day for infusing each of the patient infusions that are intended. Said recommended day is suggested by the controller in accordance with the amount of daughter radioisotope that is available in the generator on each day, so as to perform a maximal number of patient infusions. According to this embodiment, the controller will advantageously prioritize the patient infusions that require the larger amounts of daughter radioisotope during the beginning of the generator's life (when the available amount in the generator is higher) and recommend the patient infusions that require the smaller amounts of daughter radioisotope towards the end of the generator's life (when the available amount in the generator is lower). This feature of the system advantageous supports the user with the schedule of patient so as to maximize the performance of the system and the schedule.

In an embodiment of the present invention, the controller is configured to display a plan for optimizing the number of patients that will be infused during the same day, during the week, during the month or during the entire life of the generator. In an embodiment, the generator life is about 60 days. The plan preferably proposes a specific order for infusing the patients. The plan displayed by the controller, is specific for a particular day and is based on at least one of the following parameters: the quality control result, the time for establishment of the equilibrium in the generator, at least one parameter or characteristic of the patients intended for infusion on that particular day. Preferably, the parameter or characteristic of the patients that are intended for infusion on that particular day are communicated to the controller in the morning or one of the previous day. Different means can be used for communicating the information to the controller including entering the information on the user interface.

In an embodiment of the invention, the elution system further comprises a software component for predicting the recharge percentage of the generator and allow a patient infusion before complete recharge of the generator. Full recharge means that the equilibrium is reached.

In an embodiment of the invention, the elution system further comprises a valve for introducing a stress agent into the patient line and an additional pump for pumping the stress agent into the patient line. Advantageously, the pump and the valve are communicatively coupled to the controller which controls the amount of stress agent that is administered to the patient, and the time prior to the following patient elution. The controller is preferably automated to perform the calculation of the amount of stress agent that should be delivered to a patient, to deliver the stress agent to the patient, and to start the following patient elution at the optimistic time after the stress agent infusion. In an embodiment of the invention, the stress agent is dipyridamole, adenosine, adenosine triphosphate, regadenason, or dobutamine. In a preferred embodiment, the stress agent is regadenason. In another embodiment, the stress agent is administered to the patient separately, i.e. without using the elution system. Stress agent can be administered depending upon the patient parameters like age, sex, body weight, body mass index, body circumference and/or surface area. In alternate embodiments, the controller is configured to automatically calculate and infuse the stress agent dose depending upon patient characteristics at a time ranging from 5-15 minutes after rest dose administration of radiopharmaceutical.

In an embodiment of the invention, the elution system further comprises a stress agent source. In an embodiment, the stress agent infusion is performed at a predetermined time prior to infusing the daughter radioisotope eluate to the patient. In an embodiment, said pre-determined time is dependent on the nature of the stress agent.

In an embodiment of the invention, the total dose of infused radioisotope to a patient, the activity per volume, and the flow rate of the eluate are adjusted for each patient in accordance with at least one patient characteristic, such as age, sex, body weight, body mass index, body circumference or the surface area. In an embodiment, the surface area is the surface area of the region that is intended for imaging. In another embodiment, the surface area is the total surface area of a patient. Preferably, the pump is communicatively coupled to the controller to drive the eluate containing the radioisotope at a lower flow rate for infusing in a pediatric patient or a geriatric patient. A pediatric patient is a child. Preferably, a pediatric patient has below 21, or below 18 years old, or below 14 years old, or below 11 years old, or any interval between 1 day and 21 years old. A geriatric patient has above 65 years old, above 70 years old, or above 75 years old.

In an embodiment of the present invention, the pump pushes the eluant through bypass line at a certain flow rate for moving the radioactivity to the target organ of the patient rapidly after completion of elution through generator. Said flow rate is preferably higher than the flow rate for infusing the eluate containing the radioisotope, and is preferably between 10 mL/min and 100 mL/min.

In an embodiment of the invention, the controller automatically calculates the dose (total amount of radioactivity) to be infused to the patient, based on the age, sex, body weight, body mass index, body circumference and/or the surface area.

In an embodiment of the present invention, the patient is connected to a radioisotope imaging device that is arranged for imaging the patient or a region of the patient; and the elution system is connected to an imaging software of the imaging device such that the software starts the image acquisition at the pre-calculated time point. The time point is preferably 1 minute, 1.5 minute, 2 minutes, 2.5 minutes, or 3 minutes after the patient infusion has started.

In an embodiment of the invention, the daughter radioisotope is rubidium-82 ($^{82}$Rb) and the controller is connected to a software component that provides graphical output of the $^{82}$Rb activity detected by the detector at any time and pin particular during a patient elution. The software may display an alert if there is any deviation from standard activity and/or rescanning (or reimaging) the patient is required for better imaging and diagnosis.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention. Any combination of the embodiments described herein are specifically intended to be covered by the present inventors.

What is claimed:

1. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, and a controller for controlling the pump; wherein the radioisotope elution system is characterized in that:

the controller is configured to calculate a real time amount of daughter radioisotope that is available in the generator from 5 minutes to 10 minutes from the start of an establishment of an equilibrium for decay of the parent radioisotope into the daughter radioisotope;

the controller is configured to provide real time information before the establishment of the equilibrium, said real time information comprising the amount of eluted daughter radioisotope that can be infused to the patient following 5 minutes or 6 minutes from the start of the establishment of the equilibrium for decay of the parent radioisotope into the daughter radioisotope, and, the controller is configured to calculate a time that remains until the establishment of the equilibrium for decay of the parent radioisotope into the daughter radioisotope and to start a subsequent patient infusion when an available amount of the daughter radioisotope in the generator is sufficient for the patient infusion.

2. The radioisotope elution system of claim 1, wherein the real time information further comprises a flow rate of infusion that is requested to infuse said available amount, and/or a duration of infusion that is requested to infuse said available amount.

3. The radioisotope elution system of claim 1, wherein the radioisotope elution system further comprises a user interface, and wherein the controller is configured to display the real time information on the interface.

4. The radioisotope elution system of claim 3, wherein the available amount of daughter radioisotope is displayed in terms of activity dose unit.

5. The radioisotope elution system of claim 1, wherein the controller is configured to provide the real time information about the time lapsed until the establishment of the equilibrium for decay of the parent radioisotope into the daughter radioisotope.

6. The radioisotope elution system of claim 1, wherein the controller is configured to notify a user of the radioisotope elution system immediately once the available amount of daughter radioisotope reaches a needed amount that the user has entered into the radioisotope elution system.

7. The radioisotope elution system of claim 6, wherein the notification is audible or visual, or both.

8. The radioisotope elution system of claim 1, wherein a following patient infusion is pre-programmed and wherein the controller is configured to start a patient infusion corresponding to said pre-programmed patient infusion automatically when the available amount of daughter radioisotope in the generator has reached a sufficient amount for infusing the following pre-programmed patient infusion.

9. The radioisotope elution system of claim 1, wherein the daughter radioisotope is rubidium-82.

10. The radioisotope elution system of claim 1, wherein the radioisotope elution system further comprises:
  a generator line by which the eluate exits the generator;
  a tubing line that directs the eluant from the eluant reservoir to the generator,
  wherein the tubing line system comprises a first valve that directs alternatively the eluant to the generator or a bypass line,
  wherein the bypass line is merged with the generator line at a merging point;
  wherein the system further comprises a radioactivity detector downstream the merging point for detecting the radioactivity of a mixture of the daughter radioisotope eluate generated by the generator and the eluant directed by the bypass line;
  wherein the controller controls the first valve and the pump for adjusting:
    radioactivity per volume at the merging point, or
    a flow rate of the mixture at the merging point, or both.

11. The radioisotope elution system of claim 10, wherein the radioactivity per volume or the flow rate is determined in accordance with a patient requirement, wherein the patient requirement is based on at least one characteristic of the patient selected from the group consisting of age, sex, body weight, body mass index, body circumference, body surface area, and the organ or the part of the patient that is intended for imaging, wherein the organ or the part of the patient is a heart, brain, kidney, limb, or blood vessel.

12. The radioisotope elution system of claim 1, wherein the radioisotope elution system further comprises a radioisotope imaging device for imaging the patient or an organ or a part of the patient; wherein the controller is connected to an imaging software of the radioisotope imaging device.

13. The radioisotope elution system of claim 12, wherein the controller is configured to start an image acquisition at a predetermined time after the patient infusion has begun or has ended.

14. The radioisotope elution system of claim 1, wherein the radioisotope elution system further comprises a tubing system interconnecting the radioisotope elution system with a stress agent reservoir, wherein the controller is configured to control the infusion of a stress agent contained in the stress agent reservoir to the patient.

15. The radioisotope elution system of claim 14, wherein the stress agent infusion is performed at a predetermined time prior to infusing the daughter radioisotope eluate to the patient.

16. The radioisotope elution system of claim 14, wherein the stress agent infusion is automated and the controller is configured to control the dose of stress agent and the pre-determined time prior to infusing the patient with the daughter radioisotope eluate.

* * * * *